United States Patent [19]
Weber et al.

[11] Patent Number: 5,908,410
[45] Date of Patent: Jun. 1, 1999

[54] MEDICAL DEVICE WITH IMPROVED IMAGING MARKER FOR MAGNETIC RESONANCE IMAGING

[75] Inventors: Jan Weber, Roden; Christianus J. G. Bakker, Utrecht, both of Netherlands

[73] Assignee: Cordis Europa, N.V., Netherlands

[21] Appl. No.: 08/734,273

[22] Filed: Oct. 21, 1996

[30] Foreign Application Priority Data

Nov. 23, 1995 [NL] Netherlands .......................... 1001736

[51] Int. Cl.$^6$ ............................................... A61M 25/00
[52] U.S. Cl. ............................................................. 604/280
[58] Field of Search ................................... 604/280, 264, 604/281, 282

[56] References Cited

U.S. PATENT DOCUMENTS 5,045,072   9/1991   Castillo et al. .
5,171,232  12/1992   Castillo et al. .

FOREIGN PATENT DOCUMENTS

WO 87/04080   1/1987   WIPO .
WO 94/23782   4/1994   WIPO .
WO 95/21566   2/1995   WIPO .

*Primary Examiner*—John D. Yasko
*Assistant Examiner*—Manuel Mendez
*Attorney, Agent, or Firm*—Michael W. Montgomery

[57] ABSTRACT

A medical device, such as a medical catheter, having an imaging marker integral with the wall of the catheter but of a configuration such that the outer dimensions of the imaging marker remain substantially the same when the catheter is viewed along an x-axis, a y-axis and a z-axis to thereby present an image of substantially the same brightness regardless of the viewing angle.

9 Claims, 3 Drawing Sheets

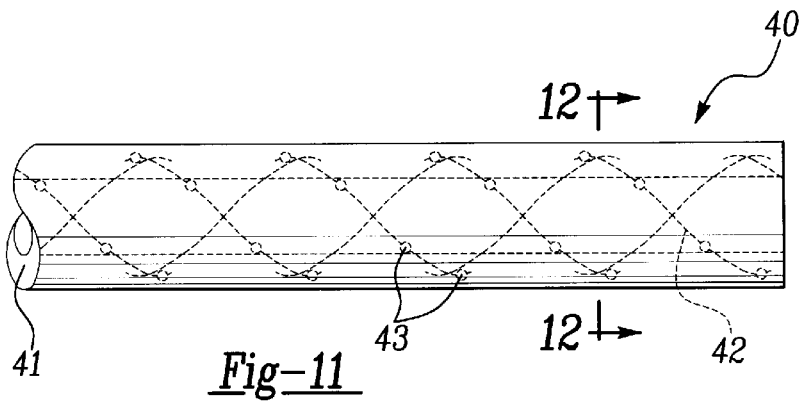
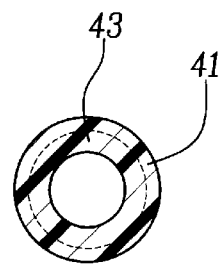
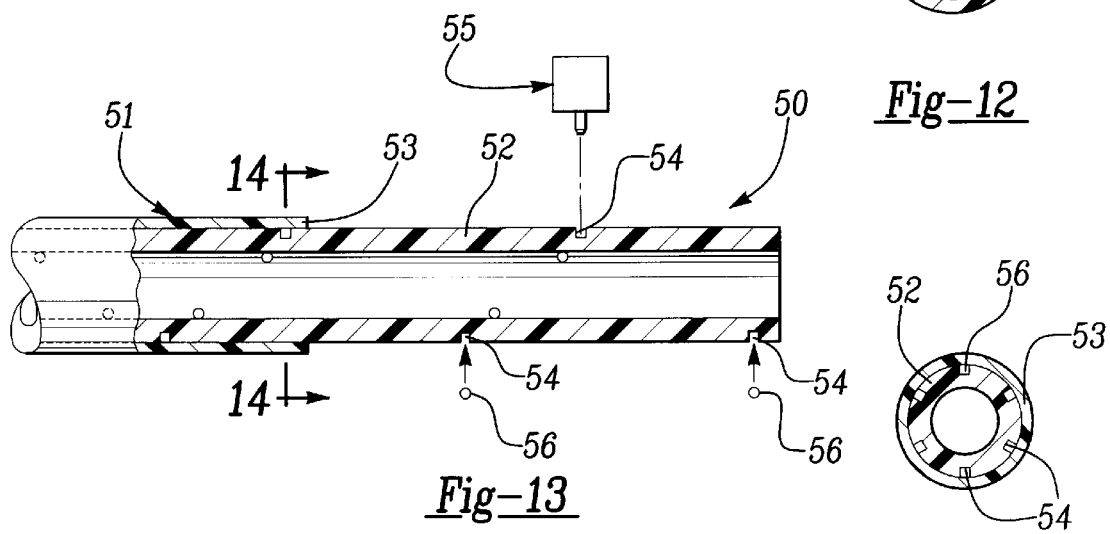
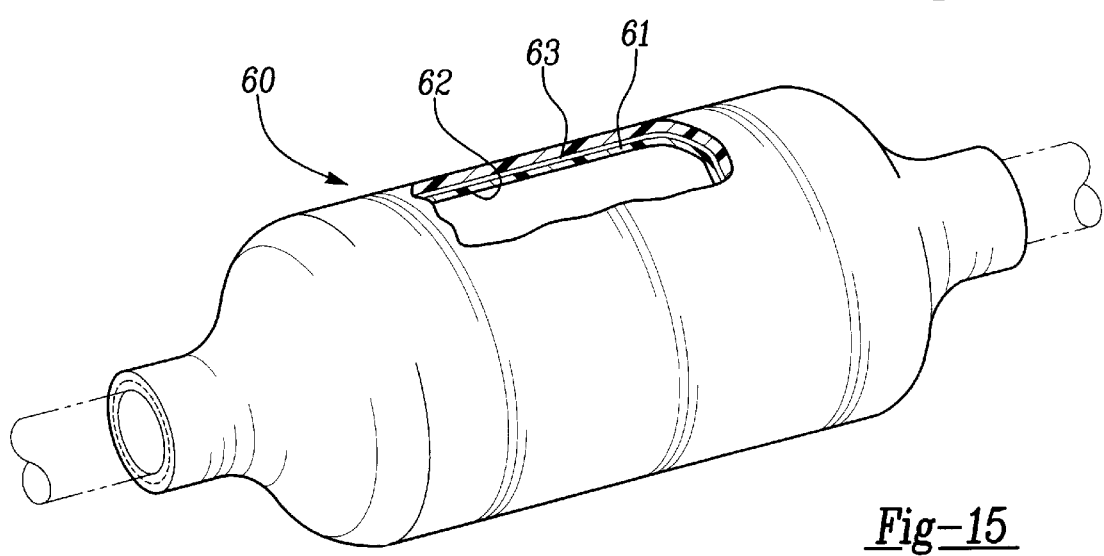

MEDICAL DEVICE WITH IMPROVED IMAGING MARKER FOR MAGNETIC RESONANCE IMAGING

FIELD OF THE INVENTION

The present invention relates to a medical device such as a catheter, but may take other forms such as a medical graft or stent, which is introduced into the body of a patient, and more particularly relates to such a device having an imaging marker for use with magnetic resonance imaging.

BACKGROUND AND DESCRIPTION OF TEE INVENTION

It is known to make medical devices, such as catheters, visible during magnetic resonance imaging by applying a paramagnetic or ferromagnetic marker band to the device. The ferromagnetic or paramagnetic materials used in the marker band disturb the magnetic field in a nuclear magnetic resonance field so as to produce a visible image on the viewing screen of a magnetic resonance imaging device.

Typically, medical catheters follow a tortuous, or winding, path as the device is inserted into the blood vessel of a subject. The distal tip of the catheter is generally flexible to avoid damage to the inner walls of the blood vessel as the catheter is passed through the vessel. The distal tip of the catheter is also generally pre-bent to a desired configuration so that the catheter may be inserted into branching blood vessels along the path. When the tip is pre-bent, the physician must be able to orient the tip so that it can be pushed into the branching blood vessels.

Representative prior art patents that disclose flexible, elongated medical catheters are U.S. Pat. No. 5,045,072 to Castillo and U.S. Pat. No. 5,171,232 to Castillo. Each of these patents, assigned to the assignee of the present invention, discloses a medical catheter in which the very distal tip of the catheter is impregnated with a radiopaque material so that when the catheter is viewed by x-ray radiation, or alternatively by fluoroscopy, the radiopaque tip is made visible so that an attending physician may view the distal tip of the catheter.

When medical catheters are used in conjunction with a magnetic resonance imaging machine, it is necessary to apply a marker band or region of a paramagnetic or ferromagnetic material to cause that band or region of the catheter to become visible under a nuclear magnetic resonance field.

One problem with currently available catheters and other medical devices which are used in a nuclear magnetic field is that as the medical device is moved or rotated to different positions within the patient so that the medical device is viewed from different angles, the level of disturbance of the magnetic field created by the magnetic material changes rather dramatically. As the surface area of the marker which is "viewed" by the magnetic resonance imaging equipment changes, i.e., increases or decreases, there is a corresponding increase or decrease in the brightness of the visual image on the viewing screen. In other words, if the medical device is rotated such that the imaging marker presents a very large surface area when "viewed" by the equipment, a very bright image appears on the imaging screen. Similarly, if the medical device is rotated to a position in which the surface area as "viewed" by the imaging device becomes very small, the image presented on the viewing screen may be either very weak or non-existent.

As may be appreciated, with the existence of a very large and intense visual image on the viewing screen it is possible that certain surrounding objects may be entirely obscured. Alternatively, if the surface area as "viewed" of the imaging marker is very small, it is possible that the visual image may be difficult, if not impossible to detect by the physician.

DISCLOSURE OF THE INVENTION

The present invention relates to a medical device, such as a medical catheter, having an imaging marker which is preferably integral with the device and in which the imaging marker produces an equal disturbance of the nuclear magnetic resonance field regardless of the position of the medical device relative to the magnetic resonance imaging equipment. In other words, the outer dimensions of the imaging marker remain substantially the same regardless of the orientation of the catheter relative to the magnetic imaging equipment. Thus, the intensity of the image presented on the imaging screen is substantially identical regardless of whether the catheter is viewed from the side of the catheter, the top of the catheter, or even the end of the catheter. With such a uniform distribution of the ferromagnetic or paramagnetic material, even an elongated device may be made uniformly visible regardless of the orientation of the device.

A medical device constructed in accordance with the present invention for use with a nuclear magnetic resonance system includes a body portion formed of a polymer material and includes at least one magnetic radiation imaging marker. The imaging marker is preferably formed of paramagnetic or ferromagnetic material. Also, the imaging marker is a configuration which exhibits the property of having substantially identical outer dimensions when the medical device is viewed by nuclear radiation imaging equipment when viewed along any one of three axes which are at right angles to each other. In other words, the outer dimensions of the imaging marker appear to be substantially identical regardless of the angle at which the medical device is "viewed" by the magnetic resonance imaging equipment. Thus, the medical device may be viewed along an x-axis, a y-axis, or a z-axis in which each of these axes extend at right angles to each other, and in each case the outer dimensions of the imaging marker remain the same when viewed by imaging equipment.

In accordance with another embodiment of the present invention, the medical device may take the form of a medical catheter in which the body portion comprises a cylindrical tube having a predetermined outer diameter and in which the radiation imaging marker extends around one-half of the circumference of the cylindrical tube and extends along the length of the cylindrical tube for a length equal to the outer diameter of the tube. With this construction, the outer dimensions of the imaging marker remain the same regardless of the orientation of the catheter relative to the imaging system.

In accordance with still another embodiment of the invention the medical catheter includes at least two magnetic radiation imaging markers in which the markers are spaced apart from each other at a distance such that there is substantially no magnetic interaction between the markers when the device is irradiated by nuclear magnetic radiation. Accordingly, each of the radiation imaging markers produces its own independent visual image which is unaffected by an adjacent marker.

In accordance with a preferred construction, the imaging markers are spaced apart from each other such that the spacing between individual markers is greater than the length of the outer dimensions of an individual imaging marker. Preferably this spacing is equal to or greater than twice the length of the outer dimensions of an individual imaging marker.

Preferably, the medical catheter is formed by extruding a cylindrical body portion by using a controlled extrusion in which polymer material is extruded without any magnetic material and then a polymer material comprising at least a portion of which includes paramagnetic or ferromagnetic material is extruded to create an imaging marker section. Another way to achieve the extrusions the alternate materials is to injection mold the body at a processing temperature which is chosen to be higher than the melting temperature of the basic polymer material but is lower than the melting temperature of the paramagnetic or ferromagnetic material. With this form of construction the granules of magnetic material remain in a matrix of the basic polymer material as separate elements.

Alternatively, holes may be drilled into the side walls of the body portion of the catheter by use of a laser beam. Each of these holes may be filled with an appropriate configuration of paramagnetic or ferromagnetic material.

Various paramagnetic and ferromagnetic materials may be selected for use in constructing the present invention. Paramagnetic materials such as dysprosium, gadolinium and alloys and salts of these materials may be used, or alternatively, ferromagnetic materials such as iron, nickel, cobalt and alloys of these materials may be used.

BRIEF DESCRIPTION OF THE DRAWINGS

FIG. 11 is a diagrammatic view illustrating an alternative version of an embodiment corresponding to FIG. 9.

FIG. 12 is a diagrammatic view illustrating a cross-sectional view along the line XII—XII of FIG. 11.

FIG. 13 is a diagrammatic view illustrating a partly cut-away section of an end of another embodiment of the invention.

FIG. 14 is a diagrammatic view illustrating a cross-section along the line XIV—XIV of FIG. 13.

FIG. 15 is a diagrammatic view illustrating a partly cut-away of a balloon catheter in accordance with the present invention.

BEST MODE FOR CARRYING OUT THE INVENTION

Figure 1:
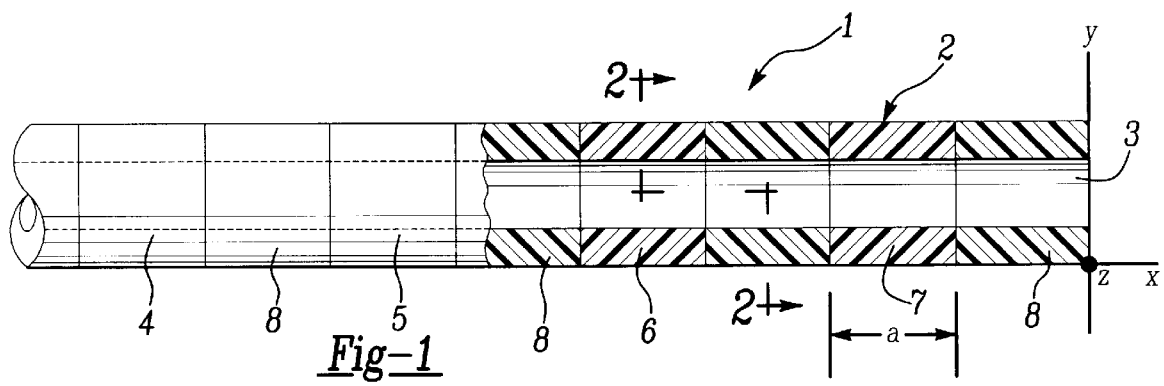
FIG. 1 is a diagrammatic view of a preferred embodiment illustrating a partly cut-away end of a medical catheter according to the invention.

The medical device 1 as shown in FIG. 1 is for instance an end-section of the cylindrical tube body 2 of a catheter. The tube body 2 comprises a lumen 3 extending through the tube body 2 in a longitudinal direction.

Figure 2:
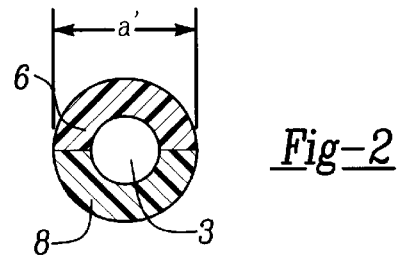
FIG. 2 is a diagrammatic view illustrating a cross-section taken along the line II—11 of FIG. 1.

As may be seen in FIGS. 1 and 2, the body 2 is made up of a number of body sections 4, 5, 6, 7 comprising paramagnetic or ferromagnetic material alternated with body sections 8 which are made of basic polymer material. The sections 4, 7 may, for instance, have been constructed by means of an injection molding process. During injection molding, the supply of basic material and the supply of the material of which the sections 4–7 are made, is formed by alternating the injection of the magnetic material into the basic material.

The sections 4–7 provided with paramagnetic or ferromagnetic material have a dimension in the longitudinal direction of the basic body 2, which is substantially equal to the diameter of the tube body. Thus, these sections form elements which have substantially equal dimensions when viewed in three directions at right angles to each other.

As a result the disturbance of a magnetic field, such as the one used with magnetic resonance imaging (MRI), caused by each of the separate elements, is at least virtually independent of the position these elements take up on this magnetic field. In other words, whether the center lines of the elements 4–7 run parallel to the magnetic field lines or are at right angles to them, the disturbance of the magnetic field and consequently the image on the screen of the resultant artefact remains more or less the same.

Figure 3:
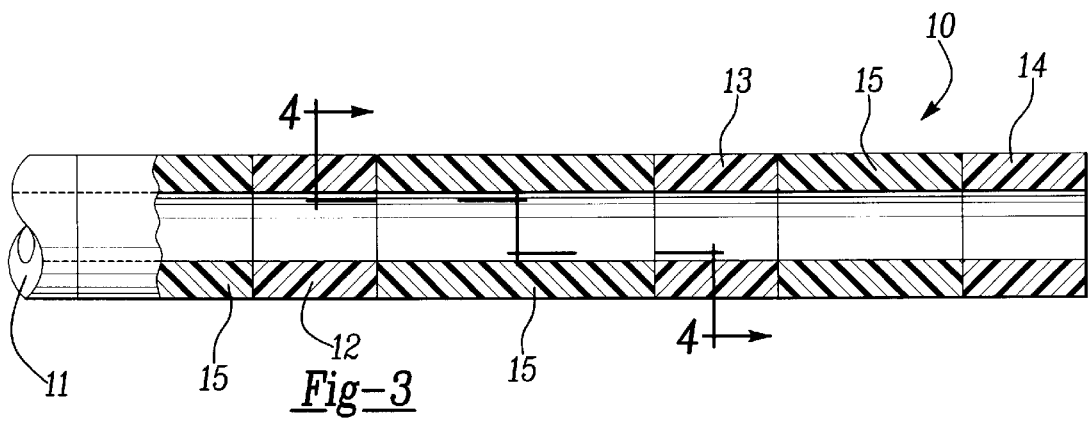
FIG. 3 is a diagrammatic view illustrating another embodiment of the invention.

The same is true for the device 10 of FIG. 3. Also in this case the elements 11, 12, 13, 14 comprising the paramagnetic or ferromagnetic material are alternated with sections 15 made of basic material. The elements 11–14 have also in this case a length which is substantially equal to the diameter of the tube body. Additionally the element 13, 14 which are positioned at the distal end of the device 10, have a greater density of paramagnetic or ferromagnetic material, so that they are more clearly visible on the screen of a magnetic imaging device.

The relative distance between the elements 4–7 of the device 1 and the elements 11–14 of the device 10 is substantially such, that there is substantially no magnetic interaction between the adjoining elements. With the embodiment of FIG. 1 the relative distance between the elements is at least equal to the length and the diameter of each of the elements 4–7, which is to say at least equal to the outer dimensions of these imaging markers. With a suitable concentration of the paramagnetic or ferromagnetic material in the elements known as such, the relative effect on each other is very small, so that the elements function as separate elements when a nuclear magnetic resonance field is applied.

With higher concentration of paramagnetic or ferromagnetic material, a greater distance is required between the separate elements in order to limit the magnetic interaction between adjacent elements.

Figure 5:
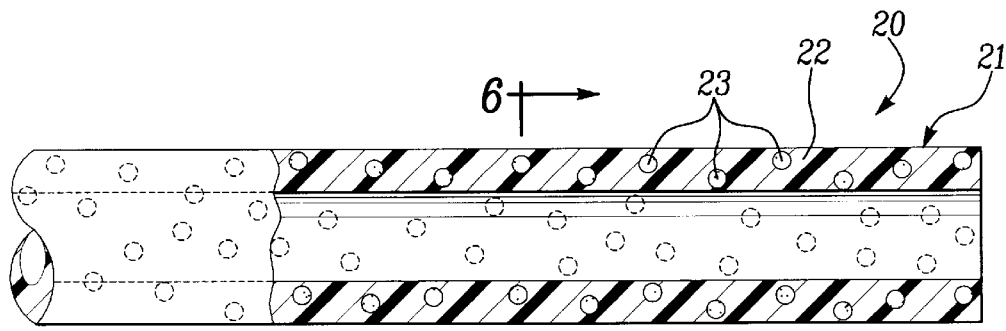
FIG. 5 is a diagrammatic view illustrating yet another embodiment of a medical catheter according to the invention.
Figure 6:
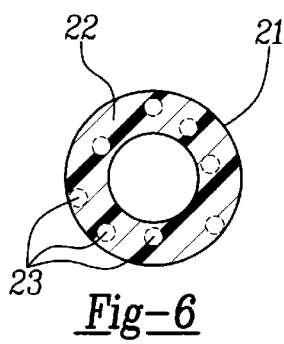
FIG. 6 is a diagrammatic view illustrating a cross-section along the line VI—VI of FIG. 5.

With the device 20 shown in FIG. 5, the basic material 22 of the body 21 is provided with a plurality of spherical elements 23 comprised of paramagnetic or ferromagnetic material. Because of the spherical shape, the disturbance of the magnetic field with these elements is also independent of the angle of the device within the magnetic field.

The imaging marker 23 may be inserted into the basic material 22 when forming the basic body 21 by means of extrusion or injection molding. In this case the elements take the form of granules of plastic material including the paramagnetic or ferromagnetic material. The magnetic material has a melting temperature which is higher than the melting temperature of the basic material 22. Thus, the elements 23 can be applied as solid particles in a flow of liquid basic material 22. Mixing the particles 23 into the basic material 22, in which case the basic material 22 is also in granular form, can be done prior to melting the material. By mixing the different granules properly, an even distribution of the elements 23 in the basic material 22 can be achieved. During the extrusion or injection molding process, a temperature is chosen at which only the granules of basic material 22 melt. The granules 23 will remain in the basic material 22 in the form of more or less solid particles.

Figure 7:
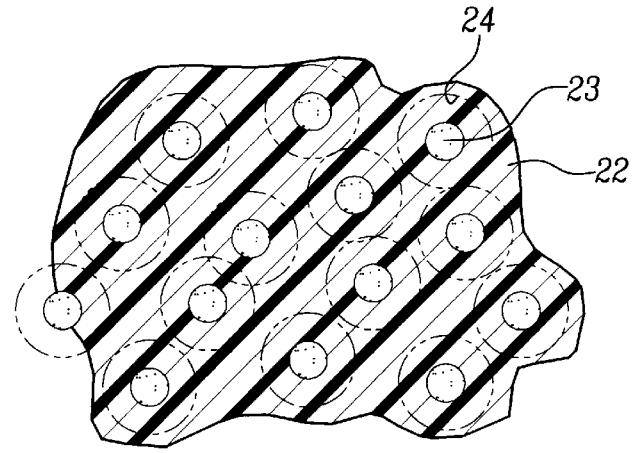
FIG. 7 is a diagrammatic view illustrating schematically another aspect of the present invention.

FIG. 7 shows schematically the importance of a suitable distance between the elements 23. With the dashed and dotted line 24, an area surrounding each element 23 has been indicated, over which the magnetic field in an magnetic imaging device may be considered to be disturbed by element 23. When the elements 23 are positioned close to each other, so that the areas 24 overlap to a significant degree, the two elements 23 would, from an image standpoint blend together so as to form one elongated element. As may be seen in FIG. 7, the elements 23 should preferably be arranged at such a distance from one another so that there is no magnetic interaction between the adjoining elements 23.

Figure 4:
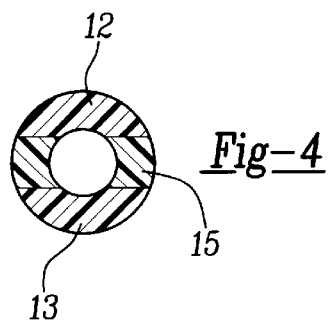
FIG. 4 is a diagrammatic view illustrating the cross-sectional view along the line IV—IV of FIG. 3.

The invention can also be employed in a suitable manner with a device according to the invention in the form of a catheter provided with a braided reinforcing layer. Such a catheter has been illustrated schematically and in a partly cut-away view in FIG. 9. The catheter 30 is made up of a first cylindrical inner layer 31, which has been extruded on a mandrel. Around this inner layer 31 a reinforcing layer of wires 33, 34 are braided. For the sake of clarity, only two wires are shown in FIG. 4, but in the usual manner there may be numerous reinforcing wires. Next, an outer layer 32 may be extruded around this braided reinforcing layer, so that the reinforcing layer is enclosed by the inner layer 31 and the outer layer 32.

Figure 8:
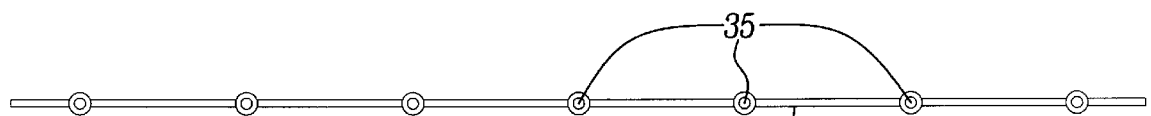
FIG. 8 is a diagrammatic view illustrating a wire provided with imaging marker.

As can be seen in greater detail in FIG. 8, the wire 34 of the catheter 30 is provided, at equal distances, with magnetic elements 35 which are substantially spherical and consequently have equal outer dimensions in three directions at right angles to one another.

Figure 9:
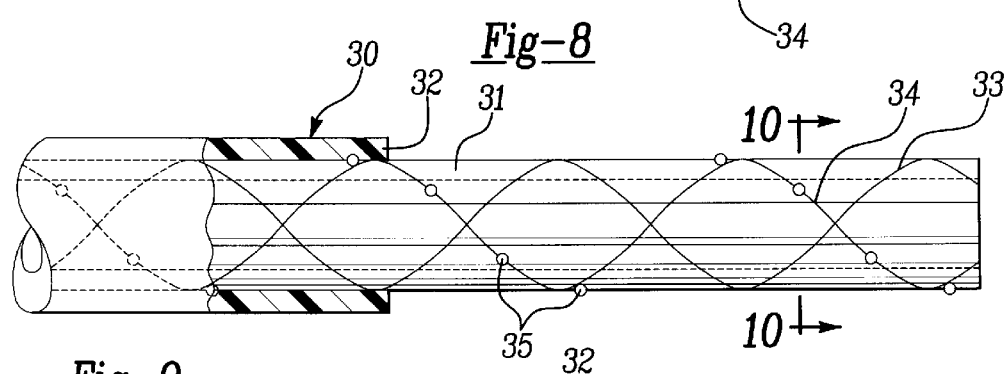
FIG. 9 is a diagrammatic view illustrating a partly broken away view of an end of a catheter according to the invention, wherein the wire of FIG. 8 has been employed in a reinforcing layer.
Figure 10:
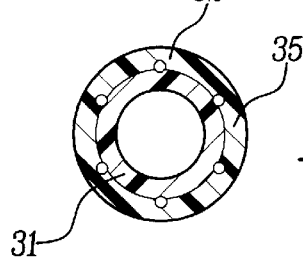
FIG. 10 is a diagrammatic view illustrating a cross-section along the line X—X of FIG. 9.

With the embodiment of FIG. 9, a satisfactory directional independency is achieved since the element 35 are positioned on a helical path. In particular, if this helical path has a pitch angle of 45°, sections of this helical arrangement which are arranged on either side opposite to each other will always be placed at right angles to one another, so that there will always be sections of the helical path which are positioned at right angles to the magnetic field.

With the device 40 of FIGS. 11 and 12, a braided layer has been co-extruded with at least one wire 42 carrying the magnetic elements 43 comprising of paramagnetic or ferromagnetic material. The device 50 of FIG. 13 comprises a tubular body 51. This tubular body 51 is made up of an inner body 52, and arranged around it, an outer layer 53. In the inner layer 52 a number of holes 54 have been formed by means of a laser device. These holes 54 are preferably arranged on a helical path. In the holes 54 formed, elements 56 have been fitted which either comprise or are made of paramagnetic or ferromagnetic material. The magnetic elements 56 are temporarily fixed in the holes 54, for instance by means of glueing. Next the inner layer 52, is provided with elements 56 and is passed through an extrusion device and provided with an outer layer 53, which consequently encloses the magnetic elements 56 in the holes 54.

Another possible embodiment of such a device is a balloon, such as the balloon 60 for use with a balloon catheter as shown in FIG. 15. This balloon is arranged on a catheter, and by means of the latter, advanced to the correct position inside the body of the patient. With the embodiment of FIG. 15 the balloon 60 comprises an outer layer 60 and an inner layer 62, which layers 60, 62 are connected to each other by means of a layer of glue 63. The layer of glue 63 comprises in this case evenly distributed granular particles of paramagnetic or ferromagnetic material. By properly mixing an adhesive and the magnetic material, the elements of magnetic material formed by these granules may be enclosed in between the outer layer 61 and the inner layer 62 of the balloon 60, placed at a suitable distance from one another, so that the balloon 60, independent of the direction of the magnetic field, can be made properly visible when using the magnetic resonance device.

Suitable materials of which to make the magnetic elements are for instance paramagnetic materials such as dysprosium and gadolinium and alloys and salts of these materials. Ferromagnetic materials which are preferably used are iron, nickel, cobalt and alloys of these materials. The concentration of the paramagnetic or ferromagnetic material used in the elements may vary from 0.001% in the case of very active ferromagnetic materials to 100% by weight of weaker magnetic materials.

The above description taken in conjunction with the attached drawings are for illustrative purposes only and are not intended to limit the scope of the invention, which is as defined in the claims below.

We claim:

1. A medical catheter for use with magnetic resonance imaging, comprising:

a body portion formed from a polymer material, and a plurality of cylindrical tubular magnetic resonance imaging markers including paramagnetic material, in which said imaging markers have constant outer and inner diameters and a constant longitudinal length, the markers being separated by and affixed to catheter body portions formed from a polymer material, such that the markers are spaced apart by a sufficient distance that there is substantially no magnetic interaction between the markers when an image of the catheter is viewed with magnetic resonance imaging equipment, wherein the length of each marker is selected such that the image of each marker has substantially the same maximum outer dimensions and is of substantially the same length and width when the catheter is viewed by magnetic resonance imaging equipment along an x-axis, a y-axis and a z-axis, in which such axes are each at right angles to each other.

2. The medical catheter as defined in claim 1, wherein the medical device includes at least two magnetic resonance imaging markers and said markers are spaced apart at a distance from each other so that there is substantially no magnetic interaction between the marker when the device is irradiated by nuclear magnetic radiation.

3. The medical catheter as defined in claim 2, wherein the spacing between the imaging markers is equal to or greater than the outer dimensions of the imaging markers.

4. The medical catheter as defined in claim 3, wherein the spacing between the imaging markers is equal to or greater than twice the outer dimensions of the imaging markers.

5. The medical catheter as defined in claim 4, wherein the imaging markers are of a length along the longitudinal axis of the catheter substantially equal to such outer diameter of the catheter.

6. An intravascular medical catheter having proximal and distal ends for use with magnetic resonance imaging, comprising:
   a body portion near the catheter distal end formed of a polymer material, the body portion defining an x-axis, a y-axis, and a z-axis which are mutually orthogonal; and
   a plurality of cylindrical tubular markers including paramagnetic material visible under magnetic resonance imaging, wherein the markers have constant outer and inner diameters and a constant longitudinal length, the markers being separated by and affixed to catheter body portions formed from a polymer material, wherein the length of each marker is selected such that each marker has substantially the same maximum outer dimensions when the body portion is viewed with magnetic resonance imaging equipment along the x-axis, y-axis, and z-axis successively, whereby each marker provides substantially the same size image regardless of perspective.

7. The medical catheter as defined in claim 6, wherein the image of each marker is of substantially the same length and width when the body portion is viewed by magnetic resonance imaging equipment along an x-axis, a y-axis, in which such axes are each at right angles to each other.

8. The medical catheter as defined in claim 7, wherein the markers are spaced apart at a sufficient distance from each other so that there is substantially no magnetic interaction between the markers when the catheter is viewed with magnetic resonance imaging equipment.

9. A medical catheter for use with magnetic resonance imaging, comprising:
   a body portion formed from a polymer material,
   a plurality of magnetic resonance imaging markers including paramagnetic material, said imaging markers each having preselected dimensions such that an image of the catheter has substantially the same maximum outer dimensions and is of substantially the same length and width, when the image of the catheter is viewed with magnetic resonance imaging equipment along each of three orthogonal axes,
   wherein said markers are spaced apart at a sufficient distance from each other so that there is substantially no magnetic interaction between the markers when an image of the catheter is viewed with magnetic resonance imaging equipment.

* * * * *